(12) United States Patent
Wang

(10) Patent No.: US 10,251,763 B2
(45) Date of Patent: Apr. 9, 2019

(54) BRAIDED SELF-EXPANDING ENDOLUMINAL STENT AND MANUFACTURING METHOD THEREOF

(71) Applicant: Lifetech Scientific (Shenzhen) Co., Ltd., Shenzhen (CN)

(72) Inventor: Yongsheng Wang, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 302 days.

(21) Appl. No.: 14/441,221

(22) PCT Filed: Nov. 6, 2013

(86) PCT No.: PCT/CN2013/086599
§ 371 (c)(1),
(2) Date: Jun. 30, 2015

(87) PCT Pub. No.: WO2014/071837
PCT Pub. Date: May 15, 2014

(65) Prior Publication Data
US 2016/0213498 A1    Jul. 28, 2016

(30) Foreign Application Priority Data

Nov. 8, 2012 (CN) .......................... 2012 1 0443878

(51) Int. Cl.
*A61F 2/89* (2013.01)
*A61F 2/90* (2013.01)
(Continued)

(52) U.S. Cl.
CPC ................. *A61F 2/89* (2013.01); *A61F 2/86* (2013.01); *A61F 2/90* (2013.01); *D04C 1/06* (2013.01);
(Continued)

(58) Field of Classification Search
CPC ................ A61F 2/90; A61F 2230/0069; A61F 2240/001
See application file for complete search history.

(56) References Cited

U.S. PATENT DOCUMENTS 4,817,613 A * 4/1989 Jaraczewski ...... A61M 25/0012
138/125
5,116,365 A * 5/1992 Hillstead ................... A61F 2/88
623/1.15
(Continued)

*Primary Examiner* — Alexander J Orkin
(74) *Attorney, Agent, or Firm* — Raymond Sun

(57) ABSTRACT

A braided self-expandable endoluminal stent comprises a tubular grid formed by connection of a plurality of wave bends in the circumferential direction. Each of the wave bands comprises a plurality of crests and troughs of an elastic wire in the axial direction, and is respectively connected with another wave band. On two sides of each of the wave bands, there is a wave band abutted thereto side by side. There is at least one cross-linking point between every two wave bands abutted side by side. Each of the cross-linking points is formed by intersecting one trough on one of the wave bands abutted side by side with one corresponding crest on the other wave band, and at least one part of the cross-linking points are fixed cross-linking points. Each of the wave bands is further staggered and overlapped with at least another wave band, and a plurality of crossing points (12, 14, 22, 23) are formed between the wave bands which are staggered and overlapped with each other. Each of the wave bands, together with at least another wave band, forms a group of parallel wave bands. As the wave bands in this group are similar in wave shape and in parallel to each other, no cross-linking points or crossing points (12, 14, 22, 23) will be formed between the parallel wave bands.

2 Claims, 6 Drawing Sheets

(51) Int. Cl.
  *D04C 1/06* (2006.01)
  *A61F 2/86* (2013.01)
(52) U.S. Cl.
  CPC . *A61F 2230/0069* (2013.01); *A61F 2240/001* (2013.01); *A61F 2250/001* (2013.01); *D10B 2509/06* (2013.01)

(56) References Cited

U.S. PATENT DOCUMENTS

| | | | | | |
|---|---|---|---|---|---|
| 5,366,504 | A | * | 11/1994 | Andersen | A61F 2/04 606/194 |
| 5,476,508 | A | * | 12/1995 | Amstrup | A61F 2/90 606/191 |
| 5,718,159 | A | * | 2/1998 | Thompson | A61F 2/06 623/1.53 |
| 6,063,113 | A | * | 5/2000 | Kavteladze | A61B 17/0057 606/200 |
| 6,187,036 | B1 | * | 2/2001 | Shaolian | A61F 2/90 623/1.1 |
| 2002/0022875 | A1 | * | 2/2002 | Strecker | A61F 2/90 623/1.15 |
| 2002/0147489 | A1 | * | 10/2002 | Hong | A61F 2/90 623/1.2 |
| 2003/0040789 | A1 | * | 2/2003 | Colgan | A61F 2/90 623/1.11 |
| 2003/0114922 | A1 | * | 6/2003 | Iwasaka | A61F 2/86 623/1.16 |
| 2003/0191517 | A1 | * | 10/2003 | Osborne | A61F 2/07 623/1.13 |
| 2004/0029478 | A1 | * | 2/2004 | Planck | A61F 2/0063 442/318 |
| 2004/0098099 | A1 | * | 5/2004 | McCullagh | A61F 2/90 623/1.15 |
| 2005/0192581 | A1 | * | 9/2005 | Molz | A61B 17/842 606/74 |
| 2005/0288775 | A1 | * | 12/2005 | Dong | A61F 2/07 623/1.54 |
| 2006/0265052 | A1 | * | 11/2006 | You | A61F 2/07 623/1.22 |
| 2007/0016283 | A1 | * | 1/2007 | Greenhalgh | A61F 2/07 623/1.15 |
| 2008/0167709 | A1 | * | 7/2008 | An | A61F 2/90 623/1.22 |

* cited by examiner

BRAIDED SELF-EXPANDING ENDOLUMINAL STENT AND MANUFACTURING METHOD THEREOF

TECHNICAL FIELD

The present invention relates to a medical instrument for supporting or repairing human vessels, in particular to a braided self-expanding endoluminal stent for endoluminal interventional treatment of arterial stenosis or occlusion and a manufacturing method thereof.

BACKGROUND OF THE INVENTION

Human vessels includes arteries, veins, tracheae, bronchi, esophagi, bile ducts, urethras, etc, the diameters of which vary from several millimeters to a few tenths of millimeters. Those human vessels may have various diseases, for example, collapse, occlusion and damage, and corresponding endoluminal stents may be used for treating those endoluminal diseases. Those endoluminal stents should satisfy some common requirements. For example, they may be encapsulated into tiny sheathes, delivered into human vessels and then released, expanded and then supported at the predetermined endoluminal positions, for the purpose of treatment.

As arteries are more likely to have diseases than other human vessels, endoluminal stents are most commonly used for treating arterial diseases. There are many kinds of arteries, typically circumferential arteries, mainly including carotid artery, subclavian artery, lower extremity artery, renal artery, etc. Arterial stenosis or occlusion is mainly caused by atherosclerosis, arteritis, fibromuscular dysplasia, etc. In western countries, about 90% arterial stenosis diseases are caused by atherosclerosis, and in China, arteritis is the common cause of arterial stenosis.

Carotid artery stenosis may result in ischemic syndromes in the head and eyes, for example, dizziness, headache, syncope, temporary amaurosis, blindness, etc. Sudden onset of subclavian arterial occlusion is usually followed by sudden limb pain, skin temperature drop, skin color change and even limb amputation if severe; and, subclavian arterial stenosis is usually followed by weakness, numbness, cold of limb, and intermittent limb pain after activities. Renal arterial stenosis is likely to result in renal arterial dysfunction. Sudden onset of lower limb arterial occlusion will result in sudden limb pain, skin temperature drop, skin color change, pale skin, and even limb amputation if severe; and lower limb arterial stenosis is usually followed by weakness, numbness, cold of limb, and intermittent limb pain after activities.

At present, there are the following methods for treating arterial stenosis.

For patients suffering from slight arterial stenosis or patients having no clinical symptoms, medical drug therapy may be adopted which, however, does not work for patients with severe symptoms. The physician will make a therapeutic scheme according to the situation of a patient, including drugs for regulating lipid and dropping blood pressure. Some patients may further need to use anticoagulant drugs to reduce the danger of causing thrombus in stenotic arteries by the blood.

For those suffering from severe arterial stenosis or complete occlusion, surgical treatment may be adopted. For an artery having a diameter of 4 to 18 millimeters, the surgical treatment is bypass operation, i.e., arterial bypass grafting. That is, the diseased stenotic arterial segment is bypassed and normal vessels at its two ends are connected by a new path. However, surgical operation causes big injuries and has many complications.

Arterial thrombolysis and thrombectomy are applicable to acute iliofemoral artery thrombus or embolism patients, however, are not applicable to chronic vessel stenosis or occlusion lesions.

For transluminal coronary angioplasty, Dotter and Judkins first conducted percutaneous angioplasty by a coaxial nylon balloon dilating catheter in 1964, which was the beginning of balloon percutaneous transluminal angioplasty (PTA). With the development of transluminal angioplasty, minimally-invasive therapy is being increasingly applied. Different from the traditional operations, transluminal coronary angioplasty has become a main treatment method for arterial stenosis or occlusion as it causes minimal injury and offers quick postoperative recovery.

At present, there are mainly two types of transluminal coronary angioplasties, one of which is balloon percutaneous transluminal angioplasty (PTA), and the other is stent implantation. Balloon percutaneous transluminal angioplasty is to expand the diseased vessel by a balloon in order to dredge the vessel. In spite of good effects in the short term, balloon percutaneous transluminal angioplasty has a high incidence of complications mainly including plaque or detachment of thrombus which causes embolism of distal vessels. Additionally, the incidence of vessel restenosis after angioplasty is high. Stent implantation is to implant a vascular stent at the diseased vessel position to expand the vessel at the diseased position. After the stent is implanted, there is a certain radial support which reduces the possibility of vessel restenosis. At present, there are mainly two kinds of stents for circumferential vessels; i.e., balloon-expandable stents and self-expanding stents. For a balloon-expandable stent, it is expanded by a balloon and has a certain radial support force due to plastic deformation. Such a stent, although accurate in positioning due to small axial shortening after expansion, is poor in its flexibility and thus is just applicable to be placed in a flat vessel; furthermore, the incidence of restenosis is higher than for self-expanding stents. For a self-expanding stent, it can automatically return to its original shape by virtue of its own super-elasticity and shape memory characteristic after being released from the sheath. Self-expanding stents have been widely applied due to their excellent performance and fewer complications, and are more applicable to vessels on the limbs (which are often in bending motion) than balloon-expanding stents. In the prior art, self-expandable stents for circumferential vessels are almost entirely made of nickel-titanium canals by laser engraving, and only a few of the self-expandable stents are braided from nickel-titanium alloy wires.

At present, self-expandable endoluminal stents are almost always laser-engraved stents; that is, are stents formed by laser-engraving nickel-titanium alloy tubes and then thermally treating those tubes for shaping. Self-expanding endoluminal stents manufactured in this way are not applicable to be bent in human endoluminal positions having activities to some extent, due to their poor flexibility and high occurrence of fatigue fracture.

There are self-expandable endoluminal stents braided from nickel-titanium wires, and self-expanding endoluminal stents braided from nickel-titanium wires are applic able to be placed at diseased and bent human endoluminal positions having activities to some extent due to their excellent flexibility and fatigue resistance. However, the braided self-expandable endoluminal stents in the prior art are quite high in axial shortening; that is, after an endoluminal stent previously compressed in the sheath is released from the sheath, the length of the endoluminal stent after it automatically expands is significantly shortened. Such shortening will result in difficulties in the positioning and control of the stent during the release process; and, the radial support force of the stent is reduced and the stent is likely to experience displacement.

SUMMARY OF THE INVENTION

Technical Problems

The present invention provides a braided self-expandable endoluminal stent to solve the problems of the braided stents in the prior art; for example, difficulties in positioning, small radial support force of the stent, and easy displacement due to shortening, and to avoid the problem that common laser-engraved endoluminal stents are likely to have fatigue fracture at tortuous positions and moveable positions of human vessels.

Solutions

Technical Solutions

The present invention employs the following technical solution to solve the technical problems. A braided self-expandable endoluminal stent is provided, including a tubular grid formed by a plurality of axial wave bands connected together along the circumferential direction, the tubular grid having a central axis, a proximal end and a distal end, each of the wave bands comprising a plurality of alternate crests and troughs wound by an elastic filament in the axial direction, the proximal end and the distal end of each of the wave bands being respectively connected to another wave band; on either side of each of the wave bands, there is a wave band abutted thereto side by side; there is at least one cross-linking point between every two wave bands abutted side by side, each of the cross-linking points is formed by intersecting one trough on one of wave bands abutted side by side with one corresponding crest on the other wave band, and at least part of the cross-linking points are fixed cross-linking points; each of the wave bands is further overlapped with at least another wave band, and a plurality of crossing points are formed between the wave bands which are overlapped with each other; each of the wave bands, together with at least another wave band, forms a group of parallel wave bands; and as the wave bands in this group are similar in wave shape and in parallel to each other, neither cross-linking points nor crossing points will be formed between the parallel wave bands.

As a further improvement of the present invention, the tubular grid comprises a plurality of crossing segments connected to each other in the axial direction, each of the crossing segments is tubular and comprises a plurality of crossing points distributed substantially uniformly, and the cross-linking points are only located on a boundary of two adjacent crossing segments, this boundary being a closed loop.

As a further improvement of the present invention, there are nk−1 cross-linking points or nk+1 cross-linking points on each of the boundaries, wherein, both n and k are natural numbers, n≥3 and k≥2.

As a further improvement of the present invention, the number of crossing points on each of the crossing segments is substantially an integral multiple of that of cross-linking points on each of the boundaries, the difference between the ratio of the two numbers and the nearest integer being less than 0.2.

As a further improvement of the present invention, the cross-linking points on the boundaries are all fixed cross-linking points.

As a further improvement of the present invention, the length of each of the crossing segments is equal.

As a further improvement of the present invention, the length of one of the crossing segments is an integral multiple of that of another crossing segment.

As a further improvement of the present invention, the diameter of the tubular grid varies in the axial direction.

As a further improvement of the present invention, the tubular grid comprises at least two segments different in diameter, which are connected to each other in the axial direction, each of the segments of the tubular grid comprises a plurality of wave bands, and there are cross-linking points formed between the wave bands of one of the segments of the tubular grid and the wave bands of another segment of the tubular grid.

The present invention employs another technical solution to solve the technical problem. A method for manufacturing a braided self-expanding endoluminal stent is provided, the endoluminal stent comprising a tubular grid having a central axis, a proximal end and a distal end, the manufacturing method comprising the following steps:

step 1: braiding a first group of grids for the tubular grid, the first group of grids being formed by a plurality of axial wave bands connected together, wherein each of the wave bands comprises a plurality of alternate crests and troughs wound by an elastic filament in the axial direction, and the proximal end and the distal end of each of the wave bands are individually connected to another wave band;

step 2: braiding a second group of grids on the first group of grids in a staggered manner, the structure and shape of the second group of grids being similar to those of the first group of grids, the second group of grids being staggered by an angle in the circumferential direction with respect to the first group of grids to form a plurality of crossing points, the elastic filament for the first group of grids being connected to the elastic filament for the second group of grids; and step 3: braiding the rest part of the tubular grid: lengthening the elastic filament for the second group of grids and connecting it to the first group of grids, and braiding the rest part of the tubular grid with the lengthened elastic filament.

As a further improvement of the manufacturing method of the present invention, in step 3, the rest part comprises a third group of grids; the elastic filament for the second group of grids is lengthened and then connected to the first group of grids via the third group of grids, and the third group of grids are braided on the first group of grids and the second group of grids in a staggered manner with the lengthened elastic filament; and the first group of grids, the second group of grids and the third group of grids are staggered in turn along the circumferential direction and overlapped to form a plurality of crossing points.

As a further improvement of the manufacturing method of the present invention, in step 1, cross-linking points are formed between the wave bands of the first group of grids to manufacture the first group of grids into a tubular shape.

As a further improvement of the manufacturing method of the present invention, in step 1, crossing points are formed between the wave bands of the first group of grids, and a plurality of cross-linking points and a plurality of crossing points are formed between the second group of grids and the first group of grids.

The present invention further provides a self-expandable endoluminal stent manufactured according to any one of the manufacturing methods described above.

Beneficial Effects

Compared with the prior art, the present invention has the following advantages. The braided self-expandable endoluminal stent provided by the present invention uses axial wave bands and inherits the advantages of closed-loop braided endoluminal stents. For example, repeatedly positioning may be realized, that is, the stent may be withdrawn into the sheath after partially released, then to be released again after position adjustment. On the other hand, the shortening is reduced so that the stent is unlikely to experience displacement during the release process; as a result the positioning is accurate and easily controlled. Furthermore, both the flexibility and the axial strength are improved, so that the stent may bear a large bending angle without kinking or losing the radial support force. Thus, the stent may be implanted into various tortuous diseased parts of the human vasculature. The fixed cross-linking points are distributed on the circumference, thereby ensuring the radial support strength of the endoluminal stent; and crossing points are distributed in different crossing segments, thereby facilitating the improvement of the flexibility of the endoluminal stent. As the fixed cross-linking points are distributed on the boundary of the adjacent crossing segments, the crossing points alternate to the fixed cross-linking points, and there are more crossing points than fixed cross-linking points, the density of the grid is enhanced and the stability of the structure is therefore better. The coverage to the artery atherosclerotic plaque is increased, the tubular grid is allowed to be deformed appropriately, the stress and the friction force are dispersed evenly, and the shortening, the flexibility and the radial support strength are balanced.

BRIEF DESCRIPTION OF THE DRAWINGS

The present invention will be further described as below with reference to the accompanying drawings and embodiments, in which.

DETAILED DESCRIPTION OF THE INVENTION

Preferred Embodiments of the Invention

Figure 1:
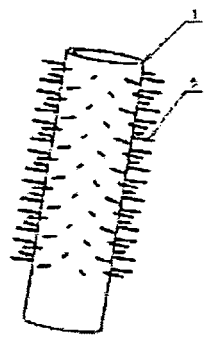
FIG. 1 is an exploded view of a pin jig for manufacturing an endoluminal stent according to the first embodiment of the present invention.

To make the objects, technical solutions and advantages of the present invention clearer, the present invention will be further described in details as below with reference to the accompanying drawings and embodiment. It should be understood that specific embodiments described here are merely used for explaining but not limiting the present invention.

The present invention provides a braided self-expandable endoluminal stent, including a tubular grid formed by a plurality of axial wave bands connected in the circumferential direction, the tubular grid having a central axis, a proximal end and a distal end, each of the wave bands comprising a plurality of alternant crests and troughs wound by an elastic filament in the axial direction, and the proximal end and the distal end of each of the wave bands being respectively connected to another wave band. On two sides of each of the wave bands, there is a wave band abutted thereto side by side respectively; there is at least one cross-linking point between every two wave bands abutted side by side, each of the cross-linking points is formed by one trough on one of wave bands abutted side by side intersected with one corresponding crest on the other wave band, and at least part of the cross-linking points are fixed cross-linking points (braiding filaments passing through any one fixed cross-linking point are intertwined and fixed with each other at this fixed cross-linking point, not capable of moving with respect to each other), each of the wave bands is further staggered and overlapped with at least another wave band, and a plurality of crossing points are formed by the wave bands which are staggered and overlapped with each other (braiding filaments passing through any one crossing point are crossed at this crossing point, capable of moving with respect to each other); each of the wave bands, together with at least another wave band, forms a group of parallel wave bands; and as the wave bands in this group are similar in wave shape and in parallel to each other, neither cross-linking points nor crossing points will be formed between the parallel wave bands.

Circumferentially-oriented sets of pins are provided on the side wall of a cylindrical mandrel, and pins respectively in two adjacent rows are arrayed in a staggered manner. A tubular grid is braided from an elastic filament (for example, nickel-titanium alloy wire) on the circumferential surface of the mandrel, and the nickel-titanium wire is wrapped around a series of pins in a predetermined order so that the characteristics of the tubular grid meet the predetermined requirements. A first wave band is wound through pins in a zigzag shape along the axial orientation of the mandrel, the wave band is wavy, and each of the axial wave bands includes a plurality of crests and a plurality of troughs alternately connected to each other; after the first wave band is completed, a second wave band is formed by the nickel-titanium alloy wire continuously winding in the zigzag shape along the opposite axial direction, and the number of the crests included in the second wave band is equal to that of the troughs included in the first wave band, and vice versa; when the crests (troughs) on the second wave band are intersected with the toughs (crests) on corresponding positions on the first wave band, the nickel-titanium wire of crests (troughs) on the second wave band is twined with the nickel-titanium wire of toughs (crests) on the first wave band, and remaining steps for braiding the second wave band are the same as those for the first wave band; and the rest wave bands are wound according to the above method. During braiding, when the nickel-titanium wire is intersected with the nickel-titanium wire of the previously braided wave band, the two nickel-titanium filaments form a crossing point or a cross-linking point here. If the two nickel-titanium wires are just crossed with each other without changing their original trends, a crossing point is formed where the nickel-titanium wires may move with respect to each other. If the two nickel-titanium wires are bent and locked together here and both nickel-titanium wires change their original trends, that is, one crest crosses one trough to be interlocked; a cross-linking point is formed where the crest and the trough are coupled in pair without disconnecting from each other. If two nickel-titanium wires at the cross-linking point are further intertwined together, a fixed cross-linking point is formed where the two nickel-titanium wires are unable to move with respect to each other. If a nickel-titanium wire successively passes through a plurality of crossing points and overlies one of the crossing points, it is better for this nickel-titanium wire overlying the adjacent crossing point (that is, passes over the other nickel-titanium wire), so repeatedly. It is better to shape the braided stent at high temperature and the tubular grid is taken off from the mandrel to obtain an endoluminal stent.

This stent is manufactured from elastic filaments, for example, nickel-titanium alloy wires, according to a stent braiding method different from those of prior art, and thus has quite low axial shortening. Hence, the release of this stent is safe and controllable, with accurate positioning. Meanwhile, sufficient radial support force is ensured, and excellent flexibility and fatigue resistance are retained.

The specific structure, manufacturing and other aspects of the endoluminal stent of the present invention will be illustrated as below by a plurality of embodiments.

The First Embodiment

Figure 2:
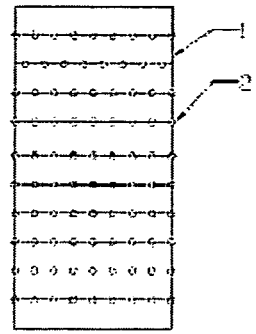
FIG. 2 is a schematic diagram of the mandrel of FIG. 1, with the outer circumferential surface unfolded.
Figure 3:
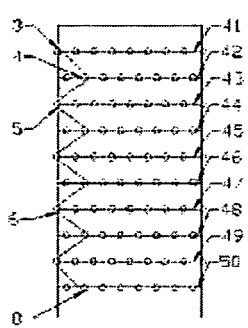
FIG. 3 is a schematic diagram showing the braiding of a first wave band of a first group of grids for the endoluminal stent according to the first embodiment of the present invention.

FIG. 1 shows a pin jig required for manufacturing this endoluminal stent. This pin jig comprises a mandrel 1 with round holes and pins 2 inserted into the round holes. On the mandrel 1, there are eight round holes in each circle along the circumferential direction of the side wall, the azimuth angle of round holes on two adjacent circumferences are staggered, and each of the pins 2 is fixed into one round hole of the mandrel 1, respectively. FIG. 2 is a schematic diagram of the mandrel 1 of FIG. 1, with the lateral surface thereof unfolded into a plane. The pins 2 are distributed evenly along the circumferences, and each of the circumferences is unfolded into a straight line. This mandrel has a total of ten circumferences in the axial direction and the distances between the adjacent circumferences are the same. Although this mandrel has ten circumferences, depending upon demands, the number of circumferences on the mandrel may be reduced to four. There may also be more than ten circumferences, and the distances between the circumferences may be different. To facilitate detailed description, after the lateral surface of the mandrel 1 in FIG. 2 is unfolded, the two pins 2 at two ends of a same circumference are shown repeatedly. Actually, the two pins shown are the same pin 2, because of the periodical array of the pins 2 on the circumferences. As shown in FIG. 2, eight pins 2 are arrayed on each circumference. In this embodiment, there may be ten pins on each circumference. In this way, a stent with uniform support force may be achieved. Generally, the number of pins on each circumference is nk−1 or nk+1, where, both n and k are natural numbers, n≥3 and k≥2. That is, in this embodiment, n=3 and k=3. When n=3 and k=2, there are five or seven pins on each circumference, and such a stent has a sparse grid. When n=4 and k=3, there are eleven or thirteen pins on each circumference, and such a stent has a dense grid which is applicable to a stent with a larger diameter. When k is an odd number, it is better to stagger the pins respectively on two adjacent circumferences. Preferably, a pin on one circumference faces a middle point of a connecting line between two adjacent pins on an adjacent circumference. In this way, the braiding of the grid will be uniform, just like the one in this embodiment. When k is an even number, it is better to enable pins respectively on two adjacent circumferences to be aligned to each other and arrayed in a matrix, in order to make the braided grid uniform. In this embodiment, a nickel-titanium wire having a diameter of 0.05 inches is used for braiding, and it may be replaced by a braiding wire made of other materials, for example, stainless steel wire. As n=3 in this embodiment, three groups of grids are to be braided, respectively. As shown in FIG. 3, a first group of grids is braided first. A first group of crest and trough (crest refers to the highest point of a wave band, and trough refers to the lowest point of a wave band) of a first wave band is winding in the axial direction, starting from the pin 3 on the first circumference 41; the filament is wrapped around the pin 4 on the second circumference 42 to form a crest; and then the filament is wrapped around the pin 5 on the third circumference 43 to form a trough. So far, the winding of the first group of crest and trough of the first wave band is completed. The nickel-titanium wire passes through the third circumference 44 and the fourth circumference 45 along a zigzag path in the axial direction according to the method mentioned above, so as to form a second group of crest and trough; then passes through the fifth circumference 46 and the sixth circumference 47 to form a third group of crest and trough; and then passes through the seventh circumference 48 and the eighth circumference 49 to form a fourth group of crest and trough. The braiding filament is wrapped around the pin 8 on the tenth circumference 50 to end the winding of the first wave band in the axial direction. The crests and troughs on one wave band are alternately arrayed, with all crests on one side of this wave band and all troughs on the other side of this wave band. For example, in the first wave band, crests are formed at positions of the pins 4 and 8 and troughs are formed at positions of the pins 5 and 6.

Figure 4:
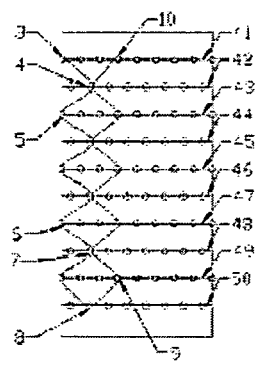
FIG. 4 is a schematic diagram showing the braiding of a second wave band of a first group of grids for the endoluminal stent according to the first embodiment of the present invention.
Figure 5:
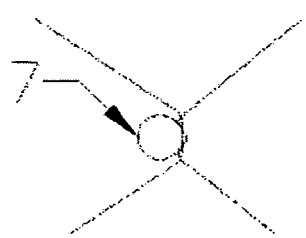
FIG. 5 is an enlarged view showing that nickel-titanium wires, intersecting at a wire hanger, are wound and fixed to each other.
Figure 6:
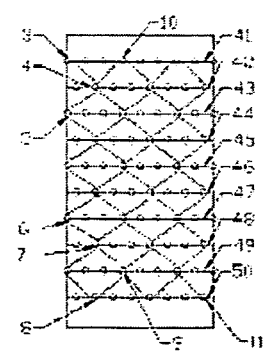
FIG. 6 is a schematic diagram of the braided first group of grids for the endoluminal stent according to the first embodiment of the present invention.

As shown in FIG. 4, the nickel-titanium wire from the pin 8 is wrapped around the pin 9 to start the winding of a first group of crest and trough of a second wave band. One trough of the second wave band is intersected with one crest in the first wave band at the position of the pin 7, and the intersected nickel-titanium wires are intertwined and fixed together at the position of the pin 7 to form one fixed cross-linking point where the braiding wires are fixed together, not capable of moving with respect to each other. FIG. 5 is a schematic diagram showing that nickel-titanium wires, intersecting in the proximity of the pin 7, are intertwined and fixed to each other. The nickel-titanium wires all change their directions after being intersected with each other, an included angle between the changed direction and the original trend is formed. In order to form a uniform grid, the included angle is preferably between 60° and 120° and kept consistent. The winding of other crests and troughs of the second wave band is completed according to the same method. A nickel-titanium wire reaches the position of the pin 10 on the first circumference 41, troughs of the second wave band are respectively intersected with crests of the first wave band to form fixed cross-linking points, and nickel-titanium wires at the intersecting positions are intertwined together. As k=3 in this embodiment, on the first circumference 41, the distance between the pin 3 and the pin 10 is three times of that between adjacent pins. That is, there are two pins reserved and unused between the pin 3 and the pin 10. The winding of the third wave band is started from the position of the pin 10, and the winding of the third, fourth and fifth wave bands is completed according to the same method. The nickel-titanium wire reaches the position of the pin 11 on the tenth circumference 50 to form the first group of grids, as shown in FIG. 6.

Figure 7:
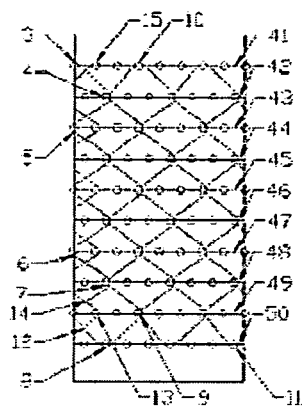
FIG. 7 is a schematic diagram showing the braiding of a second group of grids for the endoluminal stent according to the first embodiment of the present invention.

As shown in FIG. 7, the braiding of the second group of grids is started. The winding of a sixth wave band is started from the pin 11, and a first crossing point 12 between the sixth wave band and the first wave band is formed in the proximity of the pin 11. Braiding filaments passing through this crossing point are overlapped here without changing their original trends and capable of moving with respect to each other. That is, at the position of the first crossing point 12, the nickel-titanium wire of the sixth wave band meets the nickel-titanium wire of the first wave band for the first time, the nickel-titanium wire of the sixth wave band overlies the nickel-titanium wire of the first wave band, and the nickel-titanium wire of the sixth wave band and the nickel-titanium wire of the first wave band may move with respect to each other in the proximity of the first crossing point 12. Then, the nickel-titanium wire is wrapped around the pin 13 of the ninth circumference 49 to form a second crossing point 14 in the proximity of the pin 13. That is, at the position of the second crossing point 14, the nickel-titanium wire of the sixth wave band is overlapped with the nickel-titanium wire of the first wave band for the second time and passes underneath the nickel-titanium wire of the first wave band. This step is repeated, the nickel-titanium wire of the sixth wave band is crossed with the nickel-titanium wire of the second wave band for many times and alternately overlies and underlies the nickel-titanium wire of the second wave band, and when the nickel-titanium wire of the sixth wave band reaches the pin 15 on the first circumference 41, the winding of the sixth wave band is completed according to the method mentioned above. As seen, the sixth wave band is interwoven with the first waveband, and both extend in a same planar region; and the sixth wave band and the second wave band have a similar shape, and the two extend in parallel and are spaced a certain distance apart. On the first circumference 41, the pin 3 is adjacent to the pin 15, while a pin is reserved and unused between the pin 15 and the pin 10.

Figure 8:
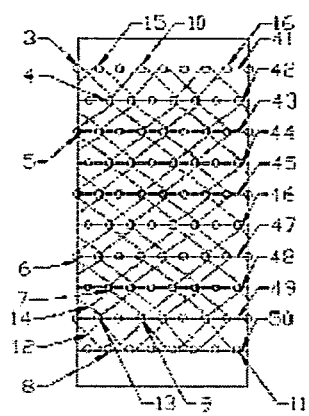
FIG. 8 is a schematic diagram of the braided first group of grids and second group of grids for the endoluminal stent according to the first embodiment of the present invention.

The winding of the seventh wave band is started from the pin 15. The nickel-titanium wire of the seventh wave band is intersected with, and alternately overlies and underlies the nickel-titanium filament of the second wave band repeatedly, to be interwoven with the second waveband. The seventh, eighth, ninth and tenth wave bands are wound according to the method mentioned above, as shown in FIG. 8. Similarly, the troughs of the seventh wave band are intertwined with corresponding crests of the sixth wave band, and the troughs of the eighth wave band are intertwined with corresponding crests of the seventh wave band, and so forth. The sixth, seventh, eighth, ninth and tenth wave bands are connected to form a second group of grids. Now, there are a total of ten wave bands woven together, so that the first group of grids and the second group of grids are intersected with each other. The position of the pin 16 is the ending point of the tenth wave band. On the first circumference 41, the pin 3 is between the pin 15 and the pin 16.

Figure 9:
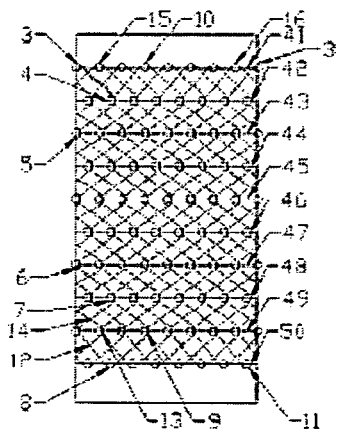
FIG. 9 is a schematic diagram of the braided endoluminal stent according to the first embodiment of the present invention.

As shown in FIG. 9, the braiding of a third group of grids is started. The winding of the eleventh wave band is started from the position of the pin 16, and the winding of the eleventh, twelfth, thirteenth, fourteenth, fifteenth and sixteenth wave bands is completed according to the method mentioned above. The position of the pin 13 is not only the ending point of the sixteenth wave band, but also the starting point of the first wave band. Starting from the position of the pin 3, the nickel-titanium wire extending from the tail of the sixteenth wave band is braided, intertwined and fixed with the nickel-titanium wire of the first wave band to form the closed third group of grids. Now, the braiding of the whole stent is finished. Therefore, the number of wave bands is exactly twice of the number of the pins. Those wave bands respectively form three groups of grids and are intersected with each other, so as to form a stent with uniform and dense grids.

Preferably, the tubular grid of the endoluminal stent includes a plurality of crossing segments connected to each other in the axial direction. Each of the crossing segments is tubular, and there is an annular and closed boundary between two adjacent crossing segments. Preferably, the grid points of each crossing segment are crossing points. As the braiding filaments in the proximity of crossing points can move with respect to each other, the crossing segments still have good flexibility even if the crossing points are dense. All the cross-linking points are distributed on boundaries between the crossing segments, and there are nk−1 or nk+1 cross-linking points on each of the boundaries, where, both n and k are natural numbers, n≥3 and k≥2. Preferably, cross-linking points on the boundaries are fixed cross-linking points. Now, the closed-ring structure of the boundaries and the fixed cross-linking points will produce a larger radial support force. Preferably, the number of crossing points of each crossing segment is substantially an integral multiple of that of cross-linking points of each boundary. As many crossing points and fixed cross-linking points may be evenly distributed in alternant regions respectively, such an endoluminal stent has excellent performance in many aspects such as axial shortening, radial support strength and flexibility.

It is better to shape the endoluminal stent, after braiding, together with the mandrel, and finally take the stent off from the mandrel. An endoluminal stent braided from nickel-titanium wires is properly thermally treated to have superelasticity.

The Second Embodiment

Figure 10:
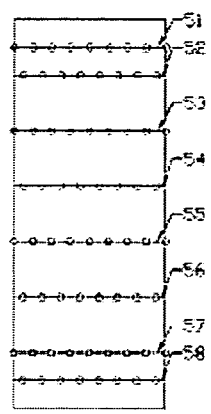
FIG. 10 is a schematic diagram of a mandrel for manufacturing an endoluminal stent according to the second embodiment of the present invention, with the outer circumferential surface unfolded.

FIG. 10 is a schematic diagram of a mandrel for manufacturing this stent, with the lateral surface unfolded into a plane, where n=3 and k=3. Different from FIG. 2, the pins 2 on the mandrel are arrayed on eight circumferences, respectively, with eight pins 2 on each of the circumferences, and the pins 2 respectively on two adjacent circumferences are staggered. The spacing between the first circumference 51 and the second circumference 52 at one end is equal to that between the seventh circumference 57 and the eighth circumference 58 at the other end, and the axial distance between two adjacent circumferences of the rest circumferences is twice of that between two adjacent circumferences at either end. For example, the distance between the second circumference 52 and the third circumference 53, the distance between the fourth circumference 54 and the fifth circumference 55, and the distance between the sixth circumference 56 and the seventh circumference 57, are all equal.

Figure 11:
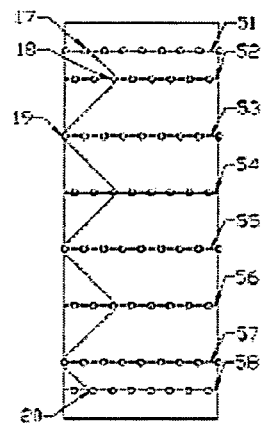
FIG. 11 is a schematic diagram showing the braiding of a first wave band of a first group of grids for the endoluminal stent according to the second embodiment of the present invention.

In this second embodiment, a nickel-titanium wire having a diameter of 0.05 inches is also used for braiding, and three groups of grids, connected to each other, are interwoven from sixteen wave bands. As shown in FIG. 11, a first group of crest and trough of a first wave band is wound in the axial direction, starting from the pin 17 on the first circumference 51, with the filament wound around the pin 18 on the second circumference 52 and then around the pin 19 on the third circumference 53, to finish the winding of the first group of crest and trough of the first wave band. The nickel-titanium wire is wound along a zigzag path in the axial direction according to the method mentioned above, wound around and terminating at the pin 20 on the eighth circumference 58, to complete the axial winding of the first wave band. In this embodiment, the bending angle of the nickel-titanium wire at each of the pins is substantially equal to that of the nickel-titanium wire at a corresponding pin as shown in FIG. 3, but due to the distance between the circumference 52 and the circumference 53 being double that of the distance between the circumference 51 and the circumference 52, the length of the nickel-titanium wire between the pin 18 and the pin 19 is double that of the nickel-titanium wire between the pin 17 and the pin 18. In other words, according to the distance that the nickel-titanium wire spans the adjacent pins, the stent is divided into a plurality of crossing segments connected to each other, and the distance between two adjacent circumferences defines the length of one crossing segment therebetween. A shorter crossing segment at one end of the endoluminal stent is braided through pins on the circumference 51 and circumference 52, five longer crossing segments in the middle of the endoluminal stent are braided through pins on and between the circumference 52 and circumference 57, and a shorter crossing segment at the other end of the endoluminal stent is braided through pins on the circumference 57 and circumference 58. By taking the spacing between the adjacent pins on a same circumference as the length unit, the pin 19 on the circumference 53 may be staggered with the pin 17 on the circumference 51 by a length unit as shown in FIG. 11 or by 1.5 times or 2 times of the length unit (not shown), in order to ensure substantially uniform grids of crossing segments with different length.

Figure 12:
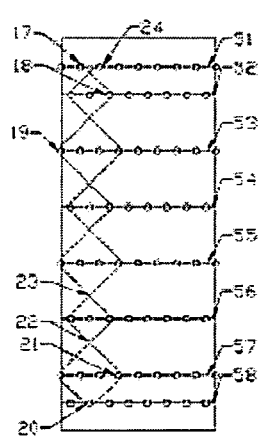
FIG. 12 is a schematic diagram showing the braiding of a second wave band of a first group of grids for the endoluminal stent according to the second embodiment of the present invention.
Figure 13:
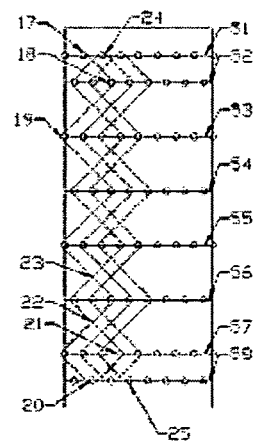
FIG. 13 is a schematic diagram of the braided first group of grids for the endoluminal stent according to the second embodiment of the present invention.

As shown in FIG. 12, the nickel-titanium wire from the pin 20 is wound around the pin 21 to start the winding of a first group of crest and trough of a second wave band. Between the circumference 56 and the circumference 57, the nickel-titanium wire of the second wave band and the nickel-titanium wire of the first wave band form a first crossing point 22. At the position of the first crossing point 22, the nickel-titanium wire of the second wave band overlies the nickel-titanium wire of the first wave band. Also, between the circumference 55 and the circumference 56, the nickel-titanium wire of the second wave band and the nickel-titanium wire of the first wave band form a second crossing point 23. At the position of the first crossing point 23, the nickel-titanium wire of the second wave underlies the nickel-titanium wire of the first wave band. This step is repeated; the nickel-titanium wire of the second wave band is intersected with the nickel-titanium wire of the first wave band repeatedly, and alternately overlies and underlies the nickel-titanium wire of the first wave band. The nickel-titanium wire is finally wound around the pin 24 on the circumference 51 according to the above winding method, to finish the winding of the second wave band. By comparing FIG. 12 and FIG. 4, an important difference between the two implementations is that, in FIG. 12 only crossing points rather than cross-linking points are formed between the first wave band and the second wave band, and nickel-titanium wires at said crossing points are not intertwined so that the first wave band and the second wave band may appropriately slide relatively to each other; while in FIG. 4, fixed cross-linking points are formed between the first wave band and the second wave band, nickel-titanium wires a are intertwined at the joints so that the first wave band and the second wave band are tightly fixed relatively to each other. For a stent with more dense grids, the braiding method as shown in FIG. 12 is easier and the braided stent has better flexibility. On the other hand, for a stent with relatively sparse grids, the braiding method as shown in FIG. 4 is useful for increasing the radial support force and for reducing the shortening. The winding of the third wave band, fourth wave band and fifth wave band is completed according to the method for winding the first wave band and second wave bands. Finally, nickel-titanium wire is wound around the pin 25 on the circumference 58, and the first, second, third, fourth and fifth wave bands are interwoven to form the first group of grids, as shown in FIG. 13.

Figure 14:
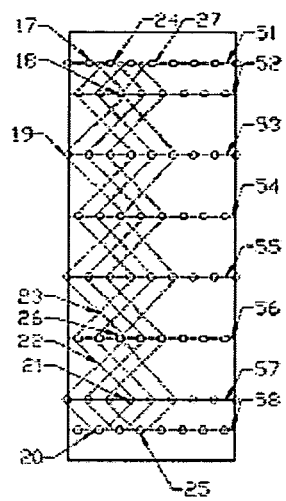
FIG. 14 is a schematic diagram showing the braiding of a second group of grids for the endoluminal stent according to the second embodiment of the present invention.

As shown in FIG. 14, the braiding of the second group of grids is started. The winding of a sixth wave band is started from the position of the pin 25, and a trough of the sixth wave band is intersected with a crest of the first wave band to form a fixed cross-linking point, and the intersected nickel-titanium wires are intertwined at the position of the pin 26. According to the above method, each of the troughs of the sixth wave band is intersected with one corresponding crest of the first wave band at the position of a corresponding pin to form a fixed cross-linking point, and the nickel-titanium wires here are intertwined. Finally the nickel-titanium wire is wrapped around the pin 27 of the circumference 51 to complete the winding of the sixth wave band. The sixth wave band has a shape similar to that of the fourth wave band, and the sixth wave band and the fourth wave band extend in parallel with a certain distance between them. However, a plurality of crossing points are formed between the sixth wave band and respective the third wave band and the fifth wave band. Therefore, there are a plurality of fixed cross-linking points formed between the sixth wave band and the first wave band in the first group of grids so that a firm joint may be formed; furthermore, there are a plurality of crossing points between the sixth wave band and the first group of grids so that they may be interwoven uniformly together.

Figure 15:
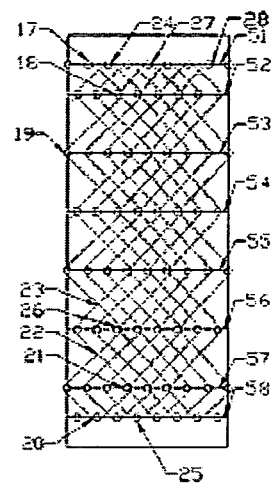
FIG. 15 is a schematic diagram of the braided first group of grids and second group of grids for the endoluminal stent according to the second embodiment of the present invention.

As shown in FIG. 15, according to the above method, the winding of the seventh wave band is started from the position of the pin 27. Each trough of the seventh wave band is intersected with a corresponding crest of the second wave band at a corresponding pin, where a fixed cross-linking point is formed. A plurality of crossing points are formed between the seventh wave band and respective the fourth wave band and the sixth wave band, and the seventh wave band and the second wave band form a relative firm connection. The winding of the eighth, ninth and tenth wave bands is continued. Now, the sixth, seventh, eighth, ninth and tenth wave bands are interwoven to form the second group of grids, and each of the wave bands is interwoven with the first group of grids, respectively. Now, there are total ten wave bands woven together so that the first group of grids and the second group of grids are intersected with each other to form more uniform crossing points. A wave band of the second group of grids and a wave band of the first group of grids are connected in pair to form a plurality of fixed cross-linking points, such as the eighth wave band and the third wave band, the ninth wave band and the fourth wave band, and the tenth wave band and the fifth wave band. Each of the connections may be accomplished by a pin where a trough of a wave band of the second group of grids is intertwined with a crest of a wave band of the first group of grids to form a fixed cross-linking point to be wound together. Hence, the second group of grids and the first group of grids form a firm multi-point connection, thereby increasing the radial support force and reducing the axial shortening of the stent.

Next, the braiding of the third group of grids is started. The winding of the eleventh wave band and the twelfth wave band shown in FIG. 15 is completed by the nickel-titanium wire being wrapped around the pin 28 on the circumference 51. Also, each trough of the eleventh wave band is respectively intersected with a corresponding crest of the sixth wave band at a corresponding pin to form a fixed cross-linking point, each trough of the twelfth wave band is respectively intersected with a corresponding crest of the seventh wave band at a corresponding pin to form a fixed cross-linking point, and the eleventh wave band and the twelfth wave band are respectively interwoven with other wave bands of the second group of grids to form a plurality of crossing points. The plurality of fixed cross-linking points formed by the eleventh wave band and the sixth wave band are fixed by intertwining, and the plurality of fixed cross-linking points formed by the twelfth wave band and the seventh wave band are fixed by intertwining, so that the third group of grids and the second group of grids form a firm and uniform connection.

Figure 16:
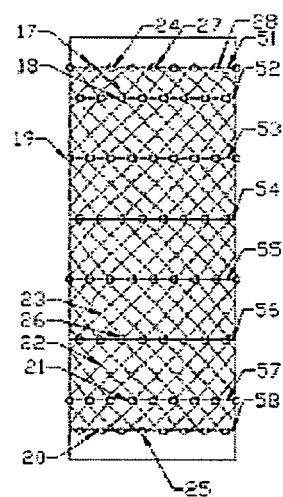
FIG. 16 is a schematic diagram of the braided endoluminal stent according to the second embodiment of the present invention.

As shown in FIG. 16, according to the above method, the braiding of the third group of grids is continued from the position of the pin 28, and the winding of the thirteenth, fourteenth, fifteenth and sixteenth wave bands is completed. Starting from the position of the pin 17, the nickel-titanium wire at the tail of the sixteenth wave band is wound and fixed with the nickel-titanium wire of the first wave band, and the braiding of the whole stent is finished. Now, the third group of grids is overlapped with the second group of grids and also with the first group of grids. For example, the thirteenth and eighth wave bands, the fourteenth and third wave bands, the fifteenth and fourth wave bands, and the sixteenth and fifth wave bands are respectively intertwined in pair to form a plurality of fixed cross-linking points. Actually, a plurality of fixed cross-linking points are formed by a wave band of the first group of grids being intertwined with a wave band of the second group of grids and with a wave band of the third group of grids respectively, and a plurality of fixed cross-linking points are formed by a wave band of the second group of grids being intertwined with a wave band of the first group of grids and with a wave band of the third group of grids respectively. Therefore, the three groups of grids are uniformly overlapped with each other to form an overall closed grid. The three groups of grids may form a uniform and firm connection of a plurality of fixed cross-linking points, and the whole grid has good long-term stability. As there are some non-intertwined crossing points formed by the three groups of grids, the three groups of grids may slide relatively to each other at those crossing points. The whole grid exhibits good short-term variability, i.e., good flexibility.

The Third Embodiment

Figure 17:
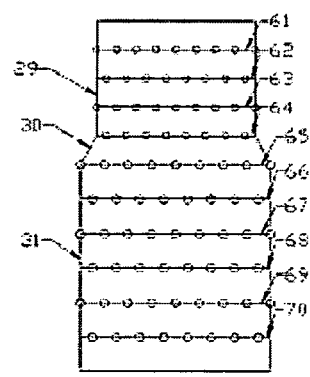
FIG. 17 is a schematic diagram of a mandrel for manufacturing an endoluminal stent according to the third embodiment of the present invention, with the outer circumferential surface unfolded.

FIG. 17 is a schematic diagram of a mandrel for manufacturing an endoluminal stent of this embodiment, with the lateral surface unfolded. This mandrel differs from the mandrel of the first embodiment in that this mandrel includes two cylindrical segments having different diameters, i.e., a small cylindrical segment 29 having a smaller diameter and a large cylindrical segment 31 having a larger diameter, which are connected to each other by a tapered segment 30 to form a mandrel with three segments as a whole. To manufacture various endoluminal stents or support members of different shapes, the shape of this mandrel may vary, for example, a multi-segment structure having an outer diameter varying like a trapezoid, a structure having a bell mouth at one or two ends, and a continuously tapered structure. By the method of braiding in segments, various endoluminal stents or support members with corresponding shapes are manufactured.

Figure 18:
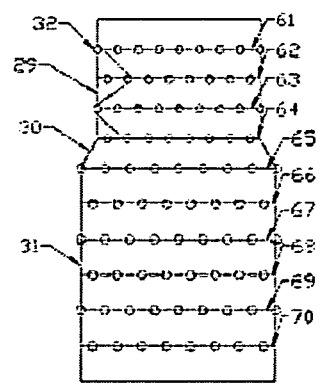
FIG. 18 is a schematic diagram showing the starting of braiding of a first segment of an endoluminal stent according to the third embodiment of the present invention.
Figure 19:
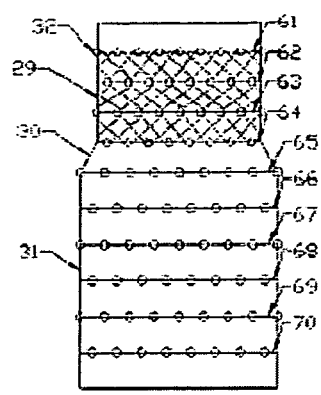
FIG. 19 is a schematic diagram of the braided first segment of the endoluminal stent according to the third embodiment of the present invention.
Figure 20:
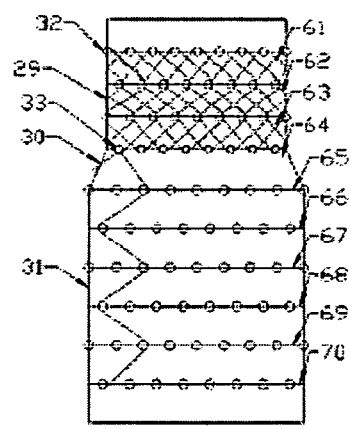
FIG. 20 is a schematic diagram showing the starting of braiding of a final segment of an endoluminal stent according to the third embodiment of the present invention.
Figure 21:
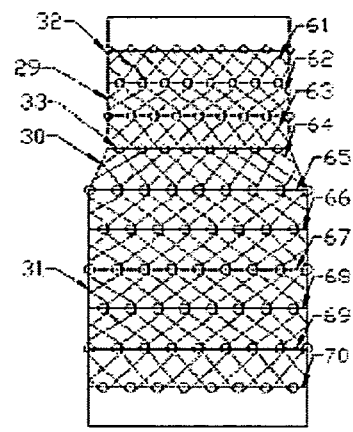
FIG. 21 is a schematic diagram of the braided endoluminal stent according to the third embodiment of the present invention.

In this embodiment, the same nickel-titanium wire as the first embodiment is used. As shown in FIG. 18 and FIG. 19, the circumferences 61, 62, 63, 64 are all on the small cylindrical segment 29, the braiding is started from the pin 32 on the circumference 61, and the braiding of the head segment of the stent is first finished on the small cylindrical segment 29 according to the same method as the first embodiment. As shown in FIG. 20, the tapered segment 30 is arranged between the circumference 64 and the circumference 65, and the circumferences 65, 66, 67, 68, 69 and 70 are all on the large cylindrical segment 31. A nickel-titanium wire is passed out from the position of the pin 33 on the circumference 64, and the braiding of the tail of the stent is started on the tapered segment 30 and the large cylindrical segment 31. To connect the tail segment of the stent to the head segment of the stent to form a completed tubular grid, when the nickel-titanium wire of the tail segment of the stent is wound around each of the pins on the circumference 64, the nickel-titanium wire is further intertwined or interlocked with the nickel-titanium wire of the head segment of the stent around this pin. If the wires are interlocked, a cross-linking point is formed and the connection between the head segment and the tail segment of the stent is relatively loosened, a fixed cross-linking point is formed if the wires are intertwined, and the stent is firmer. The resulting laddered endoluminal stent is shown in FIG. 21, the head segment of the stent has a smaller diameter and the tail segment of the stent includes a tapered transition segment and a segment having a larger diameter.

The Fourth Embodiment

Figure 22:
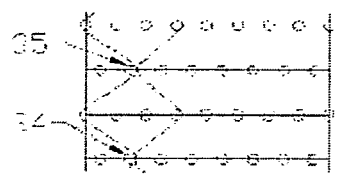
FIG. 22 is a schematic diagram of one of the fixed cross-linking points and one of the non-fixed cross-linking points of an endoluminal stent according to the fourth embodiment of the present invention.
Figure 23:
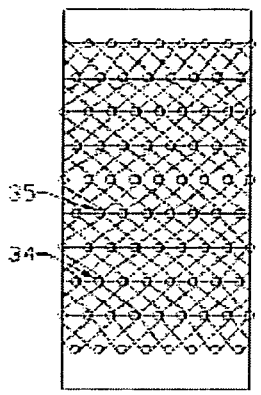
FIG. 23 is a schematic diagram of the endoluminal stent according to the fourth embodiment of the present invention, with its tubular grids including fixed cross-linking points and non-fixed cross-linking points.

In this embodiment, the same pin jig and nickel-titanium wire as the first embodiment are used. The winding of the first wave band in the axial direction is completed according to the same method as the first embodiment, and then the winding of the second wave band is started. As shown in FIG. 22, at the position of the pin 34, troughs of the second wave band are overlapped with crests of the first wave band, and the two are intertwined to form fixed cross-linking points. At the position of the pin 35, troughs of the second wave band are merely hooked up with crests of the first wave band to form a non-fixed cross-linking point, i.e., the two are interlocked, without being intertwined together. Therefore, the troughs and the crests may move relative to each other in one-way, but not be capable of disconnecting from each other. According to the method as shown in FIG. 22, the connecting points of the two wave bands are formed by interlocking and intertwining alternately, i.e., the alternate distribution of fixed cross-linking points and non-fixed cross-linking points. So far, the braiding of the second wave segment is completed. The winding of the rest wave bands is completed according to the way mentioned above. Each of the pins corresponds to one cross-linking point, and interlocking and intertwined are substantially alternately and uniformly distributed for all connecting points. That is, along the axial direction, the intertwined connecting points and the interlocked connecting points are alternately arrayed; and along the circumferential direction, the intertwined connecting points and the interlocked connecting points are also alternately arrayed; and the resulting stent is shown in FIG. 23. The endoluminal stent made according to this method has a better flexibility than stents made by purely intertwined wires. In addition, good axial shortening and uniform radial support force may be retained.

For braided self-expandable endoluminal stents in the prior art, circumferential wave bands are wound generally, and closed-ring grids are also used for increasing the radial support force. However, due to insufficient flexibility and insufficient axial strength, when it encounters resistance, such an endoluminal stent is likely to stack up and thus be shortened, and is disadvantageous for recovery to the original shape. The addition of fixed cross-linking points to the circumferential wave bands will increase the radial strength of the the endoluminal stent to a point where it is difficult to compress the stent into the sheath, which is disadvantageous for releasing and recovery of the endoluminal stent.

The advantages of the endoluminal stent of the present invention depend on the use of axial wave bands together with the inherited coherent advantages of the closed-ring braided endoluminal stent. For example, repeated positioning may be realized, that is, the stent may be withdrawn into the sheath after having been partially released, then be released again after adjustment of its position. On the other hand, the shortening is reduced so that the stent is unlikely to have displacement during the release process, thereby resulting in accurate positioning and easy control. Furthermore, both the flexibility and the axial strength are improved, so that the stent may bear a large bending angle without kinking or losing the radial support force. Thus, the stent may be implanted into various tortuous vasculatures. According to the preferred embodiment, the fixed cross-linking points are distributed on the circumference, thereby ensuring the radial support strength of the endoluminal stent; and crossing points are distributed in different crossing segments, thereby facilitating the improvement of the flexibility of the endoluminal stent. According to the preferred embodiment, as the fixed cross-linking points are distributed on the boundary of the adjacent crossing segments, the crossing points and the fixed cross-linking points are alternately distributed, and there are more crossing points than fixed cross-linking points, so the density of the grids are enhanced and the stability of the structure is thus improved. The coverage to the artery atherosclerotic plaque is increased, the tubular grid is allowed to be deformed appropriately, the stress and the friction force are dispersed evenly, and the shortening, the flexibility and the radial support strength are balanced.

For the self-expandable endoluminal stent, having a diameter of 4-12 millimeters, provided by the present invention, when the diameter is compressed by 12%, the length of the endoluminal stent is increased by only 12-18%. When the self-expanding endoluminal stent having a diameter of 8 millimeters is compressed into a sheath having an inner diameter of about 3 millimeters, the length thereof is increased by less than 40%, and the corresponding shortening is about 30%. The self-expanding endoluminal stent made according to the common braiding method in the prior art has an elongation percentage of about 100% under the same conditions and the corresponding shortening is about 50%. Therefore, compared with the braided endoluminal stents in the prior art, the shortening of the endoluminal stent of the present invention when released from the sheath is significantly reduced, which is beneficial for the controllability of operations and accuracy of positioning.

The foregoing descriptions are merely preferred embodiments of the present invention and not used for limiting the present invention. Any modifications, equivalent replacements and improvements made within the spirit and scope of the present invention should be included into the protection scope of the present invention.

The invention claimed is:

1. A method for manufacturing a braided self-expanding endoluminal stent, the endoluminal stent comprising a tubular grid having a central axis, a proximal end and a distal end, the manufacturing method comprising the following steps:

providing the grid with a plurality of spaced-apart circumferences, with each circumference having a plurality of pins provided thereon, with the number of pins along each circumference being either $nk-1$ or $nk+1$, with n being larger than or equal to 3, and k being larger than or equal to 2, braiding a plurality of groups of axial wave bands, with n being equal to the number of groups of axial wave bands, comprising the following steps:
  a. braiding a first group of axial wave bands wherein each of the wave bands comprising a plurality of alternate crests and troughs at the locations of pins wound by an elastic filament in the axial direction to form fixed cross-linking points between every two adjacent wave bands and the proximal end and the distal end of each of the wave bands are respectively connected to another wave band;
  b. braiding a second group of wave bands on the first group of wave bands, the second group of wave hands being staggered by an angle in the circumferential direction with respect to the first group of wave bands to form a plurality of crossing points where wave bands in the first group of wave bands are overlapped by wave hands in the second group of wave bands in a manner in which the filament from the second group of wave bands alternately overlies and underlies the filaments from the first group of wave bands so that the filaments of the two wave bands can move with respect to each other at the plurality of crossing points; and
  c. repeating step (b) until n groups of wave bands have been braided.

2. The manufacturing method according to claim 1, wherein each pin on one circumference faces a middle point on a connecting line between two adjacent pins on an adjacent circumference.

* * * * *